United States Patent
Riordan et al.

(12) 
(10) Patent No.: US 6,827,940 B1
(45) Date of Patent: Dec. 7, 2004

(54) IMMUNE-STIMULATING BACTERIAL CELL WALL EXTRACTS

(75) Inventors: Neil H. Riordan, Chandler, AZ (US); XiaoLong Meng, Wichita, KS (US); Hugh D. Riordan, Wichita, KS (US)

(73) Assignee: Aidan Products, LLC, Tempe, AZ (US)

( * ) Notice: Subject to any disclaimer, the term of this patent is extended or adjusted under 35 U.S.C. 154(b) by 0 days.

(21) Appl. No.: 09/579,327

(22) Filed: May 25, 2000

(51) Int. Cl.[7] ............................ A61K 45/00; C12N 1/00
(52) U.S. Cl. ................................. 424/282.1; 435/243.1
(58) Field of Search ...................... 424/282.1; 435/243.1

(56) References Cited

U.S. PATENT DOCUMENTS

| | | | |
|---|---|---|---|
| 4,515,891 A | | 5/1985 | Yokogawa et al. |
| 4,746,512 A | * | 5/1988 | Kawai et al. |
| 5,185,321 A | * | 2/1993 | Link et al. |
| 5,601,999 A | | 2/1997 | Matsuzaki et al. |
| 6,190,659 B1 | * | 2/2001 | Pancholi et al. |
| 2002/0197321 A1 | * | 12/2002 | Seager |

FOREIGN PATENT DOCUMENTS

EP 0 432 490 A2 11/1990

OTHER PUBLICATIONS

Converse et al. Lipoprotein Analysis 1992 IRL Press at Oxford University Press, pp 232–34.*
Roe et al. Protein Purification Methods 1990 IRL Press at Oxford University Press, pp 112–116 and 141–43.*

* cited by examiner

*Primary Examiner*—Mark Navarro
(74) *Attorney, Agent, or Firm*—Knobbe, Martens, Olson & Bear, LLP

(57) ABSTRACT

A method of obtaining a pharmacologically active extract of the cell walls of Gram-positive bacteria is disclosed. The method involves the treatment of the bacteria with acid such that the immune-stimulating properties are enhanced. The extracts have immune stimulating and anti-tumor activities with no toxicity at effective doses. The final products are stable, water-soluble powders.

29 Claims, 2 Drawing Sheets

IMMUNE-STIMULATING BACTERIAL CELL WALL EXTRACTS

FIELD OF THE INVENTION

The invention is generally related to methods of obtaining pharmacologically active extracts of the cell walls of Gram-positive bacteria. More particularly these extracts have immune stimulating and anti-tumor activities with no toxicity at effective doses. The final products are stable, water-soluble powders.

BACKGROUND OF THE INVENTION

Bacterial and fungal cell wall extracts have previously been used as immune stimulants and anti-tumor agents, examples are *Bacillus Calmette-Guerin* (BCG), Polysaccharide K, beta 1,3, glucan, the Maruyama vaccine, and extracts of *Bifidobacterium, L. lactis, L. fermentum, L. acidophilus* and, *S. lactis*.

Such extracts are thought to stimulate the immune system in a number of ways. One important way is to stimulate lymphocytes, well known to be involved in anti-tumor reactions in humans and animals, to grow and to produce cytokines. The cytokines produced by the lymphocytes then stimulate the immune system. For example, the cytokine interleukin-6 (IL-6) is a potent lymphoid cell growth factor that acts on B lymphocytes, and T lymphocytes. IL-6 will also act on cytotoxic T-cells in combination with other factors such as interleukin-2 (IL-2) and interferon-gamma. The cytokine interleukin-12 (IL-12) induces interferon-gamma production, enhances cytotoxic T cell responses, increases natural killer cell activity, has dramatic anti-tumor properties in a number of murine tumor models, induces regression of many established tumors, and decreases pulmonary and hepatic metastases. Therefore, the ability to induce production of such cytokines has a very powerful effect on the immune system.

All bacteria containing a cell wall, and particularly Gram positive bacteria, possess a specific component of the cell wall called peptidoglycan. The peptidoglycan provides structural support to the bacterial cell. A very early finding in the field of microbiology was that there was considerably more peptidoglycan in the Gram positive cell wall then in the Gram negative cell wall of bacteria, causing the differential Gram staining of such bacteria. The ability of the peptidoglycan to activate an immune response or act as an anti-tumor agent was a later finding in the field. Peptidoglycan is made up of alternating sugar units (N-acetylglucosamine and N-acetylmuramic acid). The sugars are joined by short peptide chains that consist of four amino acids. The sugars and tetrapeptides are crosslinked by a simple peptide bond. It is believed that the muramic acid and muramopeptides have nonspecific immunostimulatory properties, however, the exact mechanism of immunostimulation is still not clear.

U.S. Pat. No. 5,601,999 discloses an extract containing bacterial peptidoglycan which was specifically treated with a cell wall lytic enzyme. The enzyme Achromopeptidase attacks the peptidoglycan at the N-acetylmuramic acid linkages. When the extract produced with this enzyme was injected into mice with subcutaneous fibrosarcomas, the peptidoglycan extract showed a significant antitumor effect. Of course, the mechanism of the anti-tumor effect was not clear. In addition, such an extract is extremely expensive to prepare because of the treatment of peptidoglycan with the specific Achromopeptidase enzyme from *Achromobacter*.

Of interest is a peptidoglycan extract which has comparable anti-tumor effects, but is easier and less expensive to produce.

SUMMARY OF THE INVENTION

Figure 1:
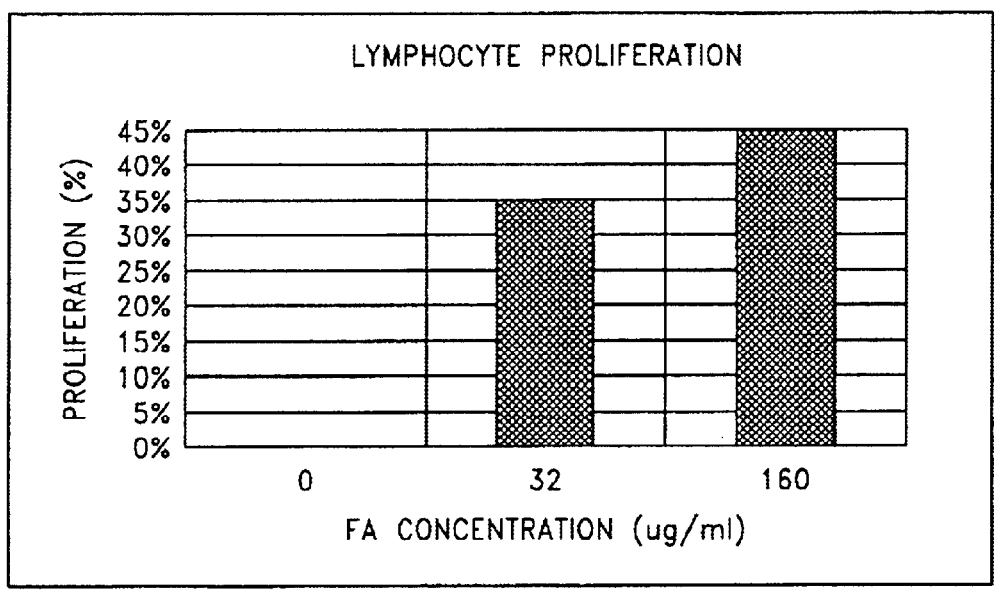
FIG. 1 is a graph showing lymphocyte proliferation in cells treated with 32 mg/ml and 160 mg/ml of a peptidoglycan extract (FA).

The general principle of the invention is to generate anti-cancer, immunostimulatory water-soluble extracts of Gram-positive bacteria such as *Lactobacillus fermentum* using an acid.

On embodiment of the invention is a method for producing an immune stimulating composition by treating a bacteria containing peptidoglycan with acid, removing large cellular components from the solution resulting from this treatment, then saving the remaining solution and adjusting the pH to a physiologically acceptable pH. Large cellular components can be removed by centrifugation, preferably at 10,000×g for about 20 minutes. The treatment with acid is preferably by heating at about 100° C., preferably for about 2 hours.

The acid used may be any acid, but is preferably selected from the group consisting of acetic acid, hydrochloric acid, and sulfuric acid, and most preferably is acetic acid. The acid treatment is preferably at a final pH of about 2.0

The bacteria containing peptidoglycan is preferably *Lactobacillus*, more preferably *L. fermentum*.

In one embodiment, the solution is also ultrafiltered to remove impurities. Lipids can be removed, preferably by treatment with chloroform; TCA precipitation can be also performed. Preferably, the remaining solution from any of the above steps is lyophilized.

A further embodiment of the invention is a method for producing a peptidoglycan extract from bacteria by heating a Gram positive bacteria in water and acid, removing large cellular particles from the solution resulting and adjusting the pH of the remaining solution to about 7.0. The acid treatment is preferably at a final pH of about 2.0. The Gram positive bacteria are preferably *Lactobacillus*.

In a further embodiment, the solution may additionally be treated to remove lipids, may be ultrafiltered, and/or TCA precipitated.

A further embodiment of the invention is a method for the treatment of cancer in a mammal by administering an effective amount of a bacterial extract, obtained as described above, in a pharmaceutically acceptable carrier. The administration can be intravenous or intraperitoneal, and the effective amount is about 900 mg/day.

A further embodiment of the invention is an immunostimulatory composition comprising the bacterial extract and a bindweed extract.

DETAILED DESCRIPTION OF THE PREFERRED EMBODIMENTS

The general principle of the invention is to generate anti-cancer, water-soluble extracts of Gram-positive bacteria such as *Lactobacillus fermentum* using an acid. A surprising result of generating such an extract was the finding that the extract has potent immunostimulatory effects (see Example 3) as well as equivalent anti-tumor effects (see Example 4).

The extract described herein is produced by extracting the bacteria (and peptidoglycan) by heating in water and acid. The crude extract is subsequently centrifuged and/or filtered to remove insoluble components. The extract can be further purified using ultrafiltration or other suitable methods for removing the reagents, salts, and other impurities prior to lyophilization to produce the final dry powder. The reconstituted powder (FA) is then used for its anti-cancer and immunostimulatory in properties. For comparison, Achromopeptidase-treated extract described in U.S. Pat. No. 5,601,999 was prepared as disclosed below, and tested as described in the following examples. The Achromopeptidase-treated extract is hereinafter referred to as FP.

Examples 1–2 provide methods for purification and production of the bacterial extract using an acid.

EXAMPLE 1

Production of FA Extract

*Lactobacillus fermentum* was grown at 37° C. in 1500-ml *Lactobacillus* MRS Broth (Fisher Scientific) for 24 hours. The broth was then centrifuged at 10,000×g for 30 minutes. The pellet was washed with 1000-ml 0.15 M NaCl resuspended in 400 ml deionized water (2-ml/gram of pellet) and 8-ml glacial acetic acid, final pH 2.0 (2% acetic acid concentration). This mixture was heated to 100° C. for 2 hours with continuous stirring. Additional water was added to maintain a volume of 400-ml. The mixture was cooled and then centrifuged at 10,000×g for 20 minutes. The supernatant was saved and the pH adjusted to 7.0 using NaOH. The pellet was retained and extracted again as above. The resulting supernatant was pooled with the first.

The pooled supernatant was ultrafiltered using a 3-KD membrane equipped stirred cell (Amicon/Millipore Corp) until the volume was reduced to 20-ml. The filter retentate was retained and mixed with 20-ml chloroform to remove lipids. This was centrifuged at 5000×g for 10 minutes, saving the upper layer. The upper portion was then heated to 100° C. with nitrogen purging to remove traces of chloroform. To the resulting solution 2.3-ml trichloroacetic acid (TCA) was added and incubated at 4° C. overnight. The solution was centrifuged at 25,000×g for 15 minutes. The supernatant was retained and pH adjusted to 7.0 using NaOH.

The resulting solution was ultrafiltered using a 3KD equipped Amicon Stir Cell until volume and was reduced to 0.5-ml. To the solution 100-ml deionized water was added and ultrafiltration continued until the volume was reduced to 5-ml. The resulting retentate was collected and lyophilized to produce the dry extract herein referred to as FA.

It is always possible that the steps of removing impurities such as lipids, DNA, RNA, and small molecular weight components are not necessary. Such steps are only necessary if there are toxic or inhibitory molecules in the crude extract. Therefore, a crude extract, FB, was prepared as described in Example 2 to analyze whether further purification steps are necessary.

EXAMPLE 2

Production of FB Extract

*Lactobacillus fermentum* was grown at 37° C. in 1000 gallons of *Lactobacillus* MRS Broth (Custom made) for 24 hours. The broth was then centrifuged at 10,000×g for 30 minutes. The pellet was resuspended in 1000 gallons of deionized water with 2% v/v acetic acid, to yield a final pH of 2.0. This mixture was heated to 100° C. for 2 hours with continuous stirring. Additional water was added to maintain a volume of 1000 gallons. The mixture was cooled and then centrifuged at 10,000×g for 20 minutes. The supernatant was saved and the pH adjusted to 7.0 using NaOH. The supernatant was retained and dried to a powder by lyophilization. The powder yielded by the supernatant is herein referred to as FB.

EXAMPLE 3

Immunostimulatory Effects

In Example 3 the immunostimulatory effect of the bacterial extract was deduced by culturing monocytes in vitro and quantitating the growth stimulation as well as the amount of IL-6 and IL-12 produced.

The extract FP was previously shown to have anti-tumor effects. One possible mechanism of those anti-tumor effects would be through stimulation of an immune cell or multiple immune cells. Therefore, in order to analyze whether the acid-treated extracts (FA and FB) have immunostimulatory activity, the effect of FA and FB on the following was examined: lymphocyte proliferation, cytokine production, and dendritic cell maturation. The protocols and results will be presented in more detail below.

To determine if the FA (and FB) extracts had anti-tumor effects, FP was used as a positive control.

The following in vitro tests were performed to analyze the immunostimulatory ability of the FA extract: In FIG. 1, the results of an experiment in which FA was added to growth medium in which lymphocytes were cultured is presented. These data show that lymphocytes did not proliferate in the control wells without addition of FA. Addition of FA at 32 micrograms/ml resulted in 35% proliferation and addition of 160 micrograms/ml resulted in 45% proliferation compared to controls, as described below.

Lymphocyte Proliferation

Human lymphocyte proliferation was analyzed as follows: human lymphocytes were collected by density gradient centrifugation from whole blood collected in EDTA anticoagulant tubes. The number of lymphocytes was determined and the cells were suspended in AIM-V culture medium with Interleukin-2 and 2-mercaptoethanol (2-ME). The cells were then equally divided into three sets and transferred to tissue culture flasks. To one third of the flasks, 32 micrograms/ml of FA was added. To one third of the flasks 160 micrograms/ml of FA was added. Nothing was added to the final third of the flasks, which served as controls. After a 3 day incubation at 37° in 95% air, 5% $CO_2$ the number of lymphocytes was compared. It was found that FA significantly induced proliferation of lymphocytes in a dose-dependent manner. See FIG. 1.

Cytokine Production

To analyze the induction of cytokine production by FA, human monocytes were collected by density gradient centrifugation from whole blood collected in EDTA anticoagulant tubes. The monocytes were resuspended in RPMI growth medium supplemented with 10% fetal calf serum. Equal numbers of monocytes in growth medium were placed into tissue culture flasks. To one third of the flasks, 0.1 mg/ml of FA was added. To one third of the flasks. 1.0 mg/ml of FA was added. Nothing was added to the final third of the flasks, which served as controls. After a 2 day incubation at 37° C. in 95% air, 5% $CO_2$, the growth media from the flasks were removed and analyzed for the concentration of interleukins-6, and -12 using ELISA assays. It was found that FA significantly increased the production of these cytokines compared to controls.

Table 1 below shows the cytokine production induced by the bacterial extract in human monocytes. FA stimulated monocytes to produce the anti-tumor cytokines, interleukin-6 and interleukin-12.

TABLE 1

FA Extract Effect on MCM Cytokines

| FA (mg/ml) | IL-6 (ng/ml) | IL-12 (pg/ml) |
|---|---|---|
| 0 | 0 | 0 |
| 0.1 | 599 | 1880 |
| 1 | 700 | 690 |

Dendritic Cell Maturation

Dendritic cells are potent antigen presenting cells that are intimately involved in the development of anti-tumor immunity. Mature dendritic cells are more potent antigen presenters than immature dendritic cells. When the supernatant from monocytes treated with 0.1 mg/ml FA (as described above in connection with the assay for cytokine production) was added to a culture of dendritic cells for a period of 3 days, the percentage of mature dendritic cells was significantly higher for the treated cells (44.8% vs. 28.1%) than the controls.

Therefore, FA was able to significantly induce lymphocyte growth, cytokine production by monocytes, and dendritic cell maturation in vitro, showing that it has potent immunostimulatory properties.

EXAMPLE 4

Anti-tumor Effect of the Bacterial Supernatant

The anti-tumor activity of FA was evaluated using the mouse S-180 tumor model. First the toxicity was determined using rats. Utilizing Karber's Method the $LD_{50}$ was calculated to be 4293 mg/kg.

The S-180 tumor model is a method routinely used in the art and is performed as follows: Tumors were induced in Kun Ming mice (mixed gender, 10/group) by implanting S-180 fibrosarcoma cells. The cells are allowed to implant for 1 to 2 days. Then the experimental agent is administered and growth of the resulting tumors follows for a given number of days.

Table 2 shows the ability of intraperitoneal and intravenous infusion of the object of this invention, FA, and the object of the Matuzaki et al. (U.S. Pat. No. 5,601,999) patent to "FP" to inhibit tumor growth inhibition in the S-180 mouse tumor model. 10 mixed male and female Kun Ming mice, 3–4 weeks old, 19–21 grams, were in each group. Mice in the "FP IP" and "FP IV" groups received 250 micrograms of an extract of L. fermentum prepared using the method described in Matuzaki et al. U.S. Pat. No. 5,601,999, intraperitoneally and intravenously, respectively, daily for 14 days, 2 days after establishment of implanted tumors. Mice in the "FA IP" and "FA IV" groups received 250 micrograms of FA intraperitoneally and intravenously, respectively at the same times as the FP groups. Control groups received an equal quantity of vehicle (saline) used in the treated groups.

After tumors were induced in mice following the above protocol, the animals were injected intraperitoneally and intravenously with FA or FP with analysis of tumor size and mass occurring on day 15. FA and FP exhibited potent anti-tumor activity in this model. The activity was similar for the two extracts, in fact, statistically ($p<0.05$) there was no difference between the ability of FP and FA to inhibit tumor growth in this model, see Table 2.

In a further experiment, FB was tested intraperitoneally as described above at a dose of 250 micrograms per injection resulting in 70% inhibition of tumor growth as compared to controls. These results show that the FB extract had the same effect as the FA and FP extracts. This is significant in that the difference between the FA and FB extracts is in the amount of purification or removal of impurities. The FB extract requires only a minimum of purification. Therefore, since the anti-tumor activity is comparable to FA, the FB extract can be used in place of the more labor-intensive FA extract.

TABLE 2

S-180 Mouse Tumor Model

| Tx (250 ug/dose) | Tumor Weight (grams) | Tumor Growth Inhibition |
|---|---|---|
| Control | 2.40 | 0% |
| FP IP | 0.60 | 75% |
| FA IP | 0.63 | 74% |
| FP IV | 0.46 | 80% |
| FA IV | 0.54 | 77% |

Given that the FA extract and the FP extract show comparable activity, it was next determined if the content of the extracts, and particularly what is thought to be the most active constituent, the peptidoglycan content, is identical. It is known that the Achromopeptidase acts on the peptidoglycan at the N-acetyl muramic acid linkages. In order to determine if the acid treatment hydrolyzes peptidoglycan comparably, gas chromatography (GC) was performed as described in Example 5 to analyze the sugar content in the extracts.

EXAMPLE 5

Composition Analysis of the Bacterial Extract

The samples were hydrolyzed using freshly prepared 1 M methanolic-HCl for 16 hours at 80° C. The released sugars were derivatized with Tri-Sil and the samples were run on GC using a Supelco column. Myo-inositol was also added (20 $\mu g$) as an internal standard.

The percentage of carbohydrate in each sample was determined to be as follows:

| FA | FP |
|---|---|
| 18.5% | 13.6% |

This is the percent of carbohydrate dissolved in the methanolic HCl and derivatized for GC-MS analysis.

TABLE 3

GC analysis of FA and FP
Mole % Carbohydrate

| | FA | FP |
|---|---|---|
| Rhamnose | — | 8.5 |
| Arabinose | 0.80 | — |

TABLE 3-continued

GC analysis of FA and FP
Mole % Carbohydrate

|  | FA | FP |
|---|---|---|
| Ribose | 0.30 | 11.2 |
| Fucose | 2.3 | — |
| Mannose | 14.0 | — |
| Galactose | 39.6 | — |
| Glucose | 40.1 | 33.0 |
| N-acetyl galactosamine | 0.5 | 16.1 |
| N-acetyl glucasamine | 2.4 | 27.2 |
| Galacturonic acid | — | 4.0 |

Therefore, as seen in Table 3, there is a structural difference in the acid treated extract of the invention and the enzyme treated extract of U.S. Pat. No. 5,601,999, suggesting that the acid cleavage occurs at different points in the peptidoglycan molecule. We have shown that the acid-treated composition has potent immunostimulatory effects in addition to the anti-tumor effects, making it useful for a wide variety of treatments. For example, it could be used to treat any illness with an immunosuppressive symptom, in addition to vaccination, in addition to treatment of an infection, or as a cancer treatment. It is interesting that the FB extract, which is very crudely purified showed equivalent anti-tumor activity to the FA extract. While the anti-tumor activity of FA (or equivalently FB) and the FP extracts was statistically the same there was, however, a clear difference in the method of making and the final product of the two extracts as shown by the gas chromatography data. In addition, the FA extract has been determined to have potent immunostimulatory activity. Thus, although considerably less expensive and easier to produce, the FA(FB) extract still provides excellent anti-tumor properties and, as shown herein, can be used in a purely immunostimulatory capacity.

Example 6 provides a protocol for the treatment of cancer patients (and other patients in need of an immunostimulatory compound).

EXAMPLE 6

Treatment with the Bacterial Extract

A standard dose of the immunostimulatory agent of the present invention is from about 0.8 to 80 mg/kg-body weight in terms of the polysaccharide-glycan complex. A patient in need of immunostimulatory treatment is injected with 900 mg/day of the FA or FB extract. Treatment is continued until a positive outcome is obtained. The extract may be used in combination with any other treatment. For example, a cancer patient presently undergoing chemotherapy or some other type of cancer treatment is additionally treated with the FA or FB extract. The treatment is continued until cancer or tumor regression or the patient is cancer free.

It is envisioned that the immunostimulatory agent could be administered in a number of different ways. For example, the agent could be taken orally. In this case, since the stomach has a pH of 1.5 to 2.5, the pH of the extract could be very low, since a pH of as low as 3 in oral medications are tolerable. Alternatively, the agent could be injected. The injectable agent could also be left at a somewhat low pH, for example, a pH of 5.3 has been shown to be tolerated. Other methods of administration and acceptable pH levels would be known to one of skill in the art.

Example 7 provides a surprisingly efficacious cancer treatment using a combination of FA and a bindweed extract (BW).

EXAMPLE 7

Combinatorial Treatment with the Bacterial Extract and Bindweed Extract

A combination of FA and a bindweed extract (BW) was tested for anti-tumor activity using the S180 tumor model. After tumors were induced in Kun Ming mice (mixed gender, 10/group), the animals were injected intraperitoneally with FA and Bindweed (the control was injected with saline) at 50 mg/kg for BW and 25 mg/kg for FA for a total of 16 days one time per day with analysis of tumor size and mass occurring on days 1, 8, 12, and 16.

The bindweed extract (*convolvulus arvensis*) was prepared as follows: Fresh *C. arvensis* was harvested and the seeds and flowers were discarded. The remaining portions of the plant were homogenized using a Waring blender. To the homogenized plant material, 3 volumes of deionized water were added to create a mixture. This mixture was then boiled for 30 minutes to obtain a tea. The solids were removed from the tea by filtration, and the supernatant retained. Low molecular weight components were removed either by TCA precipitation or by ultrafiltration. The supernatant was used for intraperitoneal treatment to assess tumor activity in this model.

Figure 2:
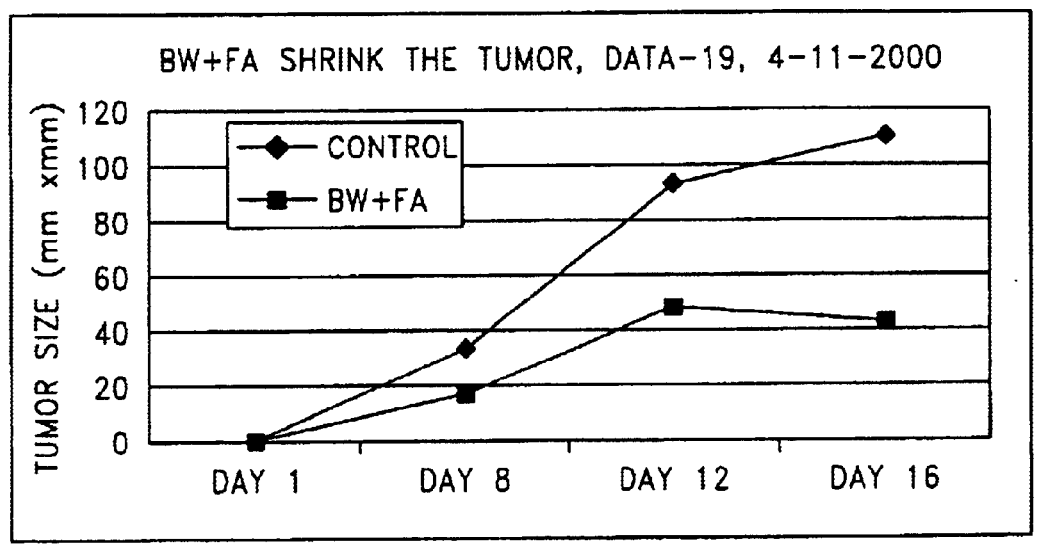
FIG. 2 is a graph showing tumor growth in mice after treatment with FA and bindweed extract.

Normally, when the S180 tumor model test is performed with the FA supernatant alone, the growth of the tumor is significantly reduced, however, the tumor does continue to grow. In FIG. 2, it can be seen that between days 12 and 16 there was actually a regression in tumor size when using the combination of FA and BW, not simply a slow-down in growth of the tumor. This indicates that the combinatorial treatment works particularly well in such a model and would be an excellent anti-tumor treatment.

TABLE 4

Combinatorial treatment

| | Tumor size (mm × mm) | | | |
|---|---|---|---|---|
| Agent | Day 1 | Day 8 | Day 12 | Day 16 |
| Control | 0 | 34.1 | 93.7 | 112.5 |
| BW + FA | 0 | 17.2 | 48.8 | 43.9 |

With reference to FIG. 2 and Table 4 the results show that the combination of bindweed extract and FA were able to actually shrink the S-180 sarcoma in the mouse in addition to inhibiting growth of the tumor. This suggests that the mixture of the two extracts has excellent cancer and immunostimulatory properties.

The embodiments described above are provided merely as examples. Changes and modification to embodiments described herein can be made by those of skill in the art without departure from the spirit and scope of the invention, as defined by the following claims.

What is claimed is:

1. A method for producing an immune stimulating composition comprising:
   treating bacteria containing peptidoglycan with an acid treatment solution;
   heating at about 100° C. during said acid treatment;
   removing insoluble components from the solution resulting from said treating;

saving the remaining solution and adjusting the pH to a physiologically acceptable pH;

testing said solution for immune-stimulating activity; and obtaining thereby an immune stimulating composition.

2. The method of claim 1 wherein said heating is for about 2 hours.

3. A method for producing an immune stimulating composition comprising:

treating bacteria containing peptidoglycan with an acid treatment solution;

removing insoluble components from the solution resulting from said treating;

precipitating said solution with trichloroacetic acid;

saving the remaining solution from said precipitation with trichloroacetic acid;

adjusting the pH to a physiologically acceptable pH;

testing said solution for immune-stimulating activity; and obtaining thereby an immune stimulating composition.

4. A method for producing an immune stimulating composition comprising:

treating bacteria containing peptidoglycan with an acid treatment solution;

removing insoluble components from the solution resulting from said treating;

saving the remaining solution and adjusting the pH to a physiologically acceptable pH;

lyophilizing said solution;

testing said lyophilized solution for immune-stimulating activity; and obtaining thereby an immune stimulating composition.

5. A method for producing an immune stimulating composition comprising:

treating bacteria containing peptidoglycan with an acid treatment solution having a final pH of about 3.0;

removing insoluble components from the solution resulting from said treating;

saving the remaining solution and adjusting the pH to a physiologically acceptable pH;

testing said solution for immune-stimulating activity; and obtaining thereby an immune stimulating composition.

6. A method for producing an immune stimulating composition comprising:

treating bacteria containing peptidoglycan with an acid treatment solution having a final pH of about 2.0;

removing insoluble components from the solution resulting from said treating;

saving the remaining solution and adjusting the pH to a physiologically acceptable pH; and obtaining thereby an immune stimulating composition.

7. A method for producing a peptidoglycan extract from bacteria comprising:

heating a Gram positive bacteria in a solution comprising water and acid at a final pH of about 2.0, wherein said solution is free of added raffinose and added enzymes;

removing insoluble particles from the solution resulting from said heating; and adjusting the pH of the remaining solution to about 7.0 obtaining thereby an immune stimulating composition.

8. The method of claim 6 wherein said bacteria containing peptidoglycan is *Lactobacillus*.

9. The method of claim 6 further comprising removing lipids from said remaining solution.

10. The method of claim 6 further comprising ultrafiltration from said remaining solution.

11. The method of claim 6 further comprising trichloroacetic acid precipitation from said remaining solution.

12. A method for producing an immune stimulating composition comprising:

treating bacteria containing peptidoglycan with an acid treatment solution having a final pH of about 2.0;

removing insoluble components from the solution resulting from said treating;

saving the remaining solution and adjusting the pH to a physiologically acceptable pH;

testing said solution for immune-stimulating activity; and obtaining thereby an immune stimulating composition.

13. The method of claim 12, wherein said immune stimulating composition is in a form suitable for injectable administration.

14. The method of claim 12 further comprising heating at about 100° C. during said acid treatment.

15. The method of claim 14 wherein said heating is for about 2 hours.

16. The method of claim 12 further comprising removing lipids from said remaining solution.

17. The method of claim 12 further comprising ultrafiltration from said remaining solution.

18. The method of claim 12 further comprising trichloroacetic acid precipitation from said remaining solution.

19. The method of claim 12 wherein said removal of insoluble components is by centrifugation.

20. The method of claim 19 wherein said centrifugation is at 10,000×g for about 20 minutes.

21. The method of claim 12 wherein said acid is selected from the group consisting of acetic acid, hydrochloric acid, and sulfuric acid.

22. The method of claim 12 wherein said acid is acetic acid.

23. The method of claim 12 wherein said bacteria containing peptidoglycan is *Lactobacillus*.

24. The method of claim 23 wherein said bacteria is *L. fermentum*.

25. The method of claim 12 further comprising ultrafiltration of said remaining solution.

26. The method of claim 12 further comprising removing the lipids from said remaining solution.

27. The method of claim 26 wherein said lipids are removed with chloroform.

28. The method of claim 12 wherein said composition has a final pH of about 5.3.

29. The method of claim 12, wherein said testing is performed by measuring at least one of the parameters selected from the group consisting of: lymphocyte proliferation, cytokine production, and dendritic cell maturation.

* * * * *